(12) United States Patent
Anagnostou et al.

(10) Patent No.: US 7,531,501 B1
(45) Date of Patent: May 12, 2009

(54) METHOD OF TREATING ENDOTHELIAL INJURY

(75) Inventors: Athanasius A. Anagnostou, Greenville, NC (US); George Sigounas, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 09/525,797

(22) Filed: Mar. 15, 2000

Related U.S. Application Data

(62) Division of application No. 08/712,358, filed on Sep. 11, 1996, now abandoned.

(51) Int. Cl.
 A61K 38/17 (2006.01)
 A61K 38/19 (2006.01)
 A61K 38/22 (2006.01)
 C07K 14/00 (2006.01)

(52) U.S. Cl. .............................. 514/2; 514/21; 530/397

(58) Field of Classification Search ................ 514/2, 514/12, 922, 21; 424/649
 See application file for complete search history.

(56) References Cited

U.S. PATENT DOCUMENTS

| 4,745,099 A | 5/1988 | Akamatsu et al. |
| 5,635,160 A | 6/1997 | Stutts et al. |

FOREIGN PATENT DOCUMENTS

| JP | 02 096535 A | 4/1990 |
| JP | 02 096535 A | 7/1990 |

OTHER PUBLICATIONS

Plantanias et al., J. Clinical Oncology, 1991, 20021-2026.*
Cazzola (Forum Trend Exp. Clin. Med., 1993, 1:344-361).*
Markham et al., Drugs, 1995, 49:232-254.*
Freshney (Culture of Animal Cells, A Manual of Basic Technique, Alan R. Liss, Inc., 1983, NY, p. 4).*
Dermer (Bio/Technology, 1994, 12:320).*
Gura (Science, 1997, 278:1041-1042).*
Wood et al, J. Clin. Invest, 1995, 95:1650-1659.*
Bokkel et al (Proc. Am. Soc. CLin. Oncol., 1994, 13, 30 Meet, 234).*
Zips et al (In vivo, 2005, 19:1-7).*

Anagnostou et al., Erythropoietin Has a Mitogenic and Positive Chemotactic Effect on Endothelial Cells, *Proc. Natl. Acad. Sci.* USA, vol. 87, pp. 5978-5982 (1990).
Cao, et al., gro-β, a-C-X-C-Chemokine Is an Angiogenesis Inhibitor That Suppresses the Growth of Lewis Lung Carcinoma in Mice, *J. Exp. Med.*, vol. 182, 2069 (1995).
Carlini et al., Effect of Recombinant Human Erythropoietin (rHuEPO) on Apoptosis in Endothelial Cells, *J. Amer. Society Nephrology*, vol. 7, No. 9, p. 1559; Abstract A1548 (1996).
Carlini, et al., Recombinant Human Erythropoietin Stimulates Angiogenesis, *Kidney International*, vol. 47, pp. 740-745 (1995).
Cazzola, M., Erythropoietin: biology and clinical applications, *Trends in Experimental and Clinical Medicine*, vol. 3, pp. 344-361 (1993).
Hand, et al., Erythropoietin Enhances Vascular Responsiveness to Norepinephrine in Renal Failure, *Kidney International*, vol. 48, pp. 806-813 (1995).
Kumar, et al, *Basic Pathology*, W. B. Saunders Company, Philadelphia, p. 194 (1992).
Kuriyama et al., Evidence for Amelioration of Endothelial Cell Dysfunction by Erythropoietin Therapy in Predialysis Patents, *Am. J. Hyperten*, vol. 9, No. 5, pp. 426-431 (1996).
Kuwata, et al., Treatment of Metastatic Liver Tumors by Intermittent Repetitive Injection of an Angiogenesis Inhibitor Using an Implantable Port System in a Rabbit Model, *Kobe J. Med. Sci.*, vol. 43, No. 2, pp. 83-98 (1997).
Livnah, et al., Functional Mimicry of a Protein Hormone by a Peptide Agonist: The EPO Receptor Complex at 2.8 Å, *Science*, vol. 273, pp. 464-471 (1996).
Maier, et al., In vitro inhibition of endothelial cell growth by the antiangiogenic drug AGM-1470 (TNP-470) and the anti-endoglin antibody TEC-11, *Anti-Cancer Drugs*, vol. 8, pp. 238 (1997).
Markham, et al., Epoetin Alfa, A Review of its Pharmacodynamic and Pharmacokinetic Properties and Therapeutic Use in Nonrenal Applications, *Drugs*, vol. 49, No. 2, pp. 232-254 (1995).
Nagai, et al., Effects of rHuEpo on Cellular Proliferation and Endothelin-1 Production in Cultured Endothelial Cells, *Nephrol Dial Transplant*, vol. 10, pp. 1814-1819 (1995).
Pluda, J.M., Tumor-Associated Angiogenesis: Mechanisms, Clinical Implications, and Therapeutic Strategies, *Seminars in Oncology*, vol. 24, pp. 203 (1997).

(Continued)

*Primary Examiner*—Karen A Canella
(74) *Attorney, Agent, or Firm*—Myers Bigel Sibley & Sajovec, PA

(57) ABSTRACT

The use of human erythropoietin (EPO) to prevent or treat endothelial injury due to chemotherapy, radiation therapy, mechanical trauma, or to a disease state which damages the endothelium (such as inflammation, heart disease or cancer) is described. The use of EPO in conjunction with the administration of chemotherapeutic agents is described.

12 Claims, 4 Drawing Sheets

OTHER PUBLICATIONS

Takano, et al., *A Diaminoathraquinone Inhibitor of Angiogenesis, J. Pharmacol. Exp. Ther.*, vol. 271, p. 1027 (1994).

Wrighton, et al., *Small Peptides as Potent Mimetics of the Protein Hormone Erythropoietin, Science*, vol. 273, pp. 458-463 (1996).

Yamaji et al., Brain capillary endothelial cells express two forms of erythropoietin receptor mRNA, *European J. Biochem.*, vol. 239, pp. 494-500 (1996).

Yamaji, et al., Brain Capillary Endothelial Cells Express Two Forms of Erythropoietin Receptor mRNA, *Eur. J. Biochem.*, vol. 239, p. 494 (1996).

Carlini et al. "Recombinant Human Erythropoietin (rHuEPO) Increases Endothelin-1 Release by Endothelial Cells" *Kidney International* 43: 1010-1014.

De Vos et al. "Endothelial cell effects of cytotoxics: balance between desired and unwanted effects" *Cancer Treat Rev* 30(6): 495-513 (Oct. 2004).

Hockel et al. "Therapeutic Angiogenesis" *Arch Surg* 128: 423-429 (1993).

M. Cazzola; "Erythropoietin: biology and clinical applications"; *Trends in Experimental and Clinical Medicine*, 3:344-361 (1993).

Miller et al. "Phase I-II Trial of Erythropoietin in the Treatment of Cisplatin-Associated Anemia" *J Natl Cancer Inst* 84(2): 98-103 (1992).

Rubins "Response to Treatment with Human Recombinant Erythropoietin" *Annals of Internal Medicine* 122(9): 676-677 (1995).

Silvestris et al. "Long-term therapy with recombinant human erythropoietin (rHu-EPO) in progressing multiple myeloma" *Ann Hematol* 70(6): 313-318 (1995).

Sungur "Renal Cell Carcinoma and Erythropoietin" *Annals of Internal Medicine* 123(9): 732-733 (1995).

Breymann et al. "Optimal timing of repeated rh-erythropoietin administration improves its effectiveness in stimulating erythropoiesis in healthy volunteers" *Br J Haematol.* 92(2):295-301 (1996).

Ito et al. "Vitamin E prevents endothelial injury associated with cisplatin injection into the superior mesenteric artery of rats" *Heart Vessels* 10(4):178-84 (1995).

Komatsumoto et al. "Multiple cerebral infarction after treatment with cisplatin" *Rinsho Shinkeigaku* 36(3):499-502 (1996).

Bukowski et al., *Phase IV evaluation of clinical outcomes of PROCRIT (Epoetin alfa) in anemic cancer patients receiving chemotherapy*, Blood, Journal of the American Society of Hematology, vol. 84, No. 10, Supp. 1, Dec. 1994, p. 129A.

Taylor et al., *Effect of nifedipine on changes in fibrinogen and von Willebrand factor in haemodialysis patients treated with recombinant human erythropoietin*, Blood Coagulation and Fibrinolysis: An International Journal in Heamostasis and Thrombosis, vol. 6, No. 2, Apr. 1995, pp. 100-104.

Taylor et al., *Effect of erythropoietin therapy and withdrawal on blood coagulation and fibrinolysis in hemodialysis patients*, Kidney International, vol. 44, No. 1, Jul. 1993, pp. 182-190.

Reinhart, *Shear-dependence of endothelial functions*, Experientia, vol. 50, No. 2, Feb. 15, 1994, pp. 87-93.

Anagnostou et al., *Erythropoietin Has a Mitogenic and Positive Chemotactic Effect on Endothelial Cells, Proc. Natl. Acad. Sci. USA*, vol. 87, pp. 5978-5982 (1990).

Cao, et al., *gro-β,a-C-X-C-Chemokine Is an Angiogenesis Inhibitor That Suppresses the Growth of Lewis Lung Carcinoma in Mice, J. Exp. Med.*, vol. 182, 2069 (1995).

Carlini et al., *Effect of Recombinant Human Erythropoietin (rHuEPO) on Apoptosis in Endothelial Cells, J. Amer. Scoiety Nephrology*, vol. 7, No. 9, p. 1559; Abstract A1548 (1996).

Carlini, et al., *Recombinant Human Erythropoietin Stimulates Angiogenesis, Kidney International*, vol. 47, pp. 740-745 (1995).

Cazzola, M., *Erthyropoietin: biology and clinical applications, Trends in Experimental and Clinical Medicine*, vol. 3, pp. 344-361 (1993).

Hand et al., *Erythropoietin Enhances Vascular Responsiveness to Norepinephrine in Renal Failure, Kidney International*, vol. 48, pp. 806-813 (1995).

International Search Report for PCT/US97/15966.

Kumar, et al, *Basic Pathology*, W. B. Saunders Company, Philadelphia, p. 194 (1992).

Kuriyama et al., *Evidence for Amelioration of Endothelial Cell Dysfunction by Erythropoietin Therapy in Presialysis Patents, Am. J. Hyperten*, vol. 9, No. 5, pp. 426-431 (1996).

Kuwata, et al., *Treatment of Metastatic Liver Tumors by Intermittent Repetitive Injection of an Angiogenesis Inhibitor Using an Implantable Port System in a Rabbit Model, Kobe J. Med. Sci.*, vol. 43, No. 2, pp. 83-98 (1997).

Livnah, et al., *Functional Mimicry of a Protein Hormone by a Peptide Agonist: The EPO Receptor Complex at 2.8 Å, Science*, vol. 273, pp. 464-471 (1996).

Maier, et al., In vitro *inhibition of endothelial cell growth by the antiangiogenic drug AGM-1470 (TNP-470) and the anti-endoglin antibody TEC-11, Anti-Cancer Drugs*, vol. 8. pp. 238 (1997).

Markham, et al., *Epoetin Alfa, A Review of its Pharmacodynamic and Pharmacokinetic Properties and Therapeutic Use in Nonrenal Applications, Drugs*, vol. 49, No. 2, pp. 232-254 (1995).

Nagai, et al., *Effects of rHuEpo On Cellular Proliferation and Endothelin-1 Production in Cultured Endothelial Cells, Nephrol Dial Transplant*, vol. 10, pp. 1814-1819 (1995).

Pluda, J.M., *Tumor-Associated Angiogenesis: Mechanisms, Clinical Implications, and Therapeutic Strategies, Seminars in Oncology*, vol. 24, pp. 203 (1997).

Takano, et al., *A Diaminoathraquinone Inhibitor of Angiogenesis, J. Pharmacol. Exp. Ther.*, vol. 271, p. 1027 (1994).

Wrighton, et al., *Small Peptides as Potent Mimetics of the Protein Hormone Erythropoietin, Science*, vol. 273, pp. 458-463 (1996).

Yamaji et al., *Brain capillary endothelial cells express two forms of erythropoietin receptor mRNA, European J. Biochem.*, vol. 239, pp. 494-500 (1996).

Yamaji, et al., *Brain Capillary Endothelial Cells Express Two Forms of Erythropoietin Receptor mRNA, Eur. J. Biochem.*, vol. 239, p. 494 (1996).

Communication with Supplementary European Search Report, EP 97 94 0974, Jul. 15, 2002.

Bukowski et al., *Phase IV evaluation of clinical otucomes of PROCRIT (Epoetin alfa) in anemic cancer patients receiving chemotherapy*, Blood, Journal of the American Society of Hematology, vol. 84, No. 10, Supp. 1, Dec. 1994, p. 129A.

Taylor et al., *Effect of nifedipine on changes in fibrinogen and von Willebrand factor in haemodialysis patients treated with recombinant human erythropoitin*, Blood Coagulation and Fibrinolysis: An International Journal in Haemostasis and Thrombosis, vol. 6, No. 2, Apr. 1995, pp. 100-104.

Taylor et al., *Effect of erythropoietin therapy and withdrawal on blood coagulation and fibrinolysis in hemodialysis patients*, Kidney International, vol. 44, No. 1, Jul. 1993, pp,. 182-190.

Reinhart, *Shear-dependence of endothelial functions*, Experientia, vol. 50, No. 2, Feb. 15, 1994, pp. 87-93.

U.S. Appl. No. 09/525,808, filed Mar. 15, 2000.

Urushizaki, I. *Domain of Chemotherapy*, 10(6):1031-1037 (1994).

Anagnostou et al., "Erthropoietin has a mitogenic and positive chemotactic effect on endothelial cells", *Proc. Natl. Acad. Sci. USA*, 87(15):5978-5982 (1990).

Fujioka et al., "Effects of recombinant erythropoietin on kidney cancer cell growth and tumor angiogenesis", *Autologous Blood Tansfusion*, 8(1):46-50 (1995).

Nagai, T., "Effects of rHuEPO on cellular proliferation and endothelin-1 production in cultured endothelian cells", *J. of Japanese Soc. Of Nephrology*, 36(3):194-200 (1994).

Japanese Office Action corresponding to Japanese Patent Application No. 513794/1998 mailed Aug. 28, 2007.

Interlocutory Decision in Opposition Proceedings corresponding to European Patent No. 0933995 dated Oct. 13, 2008.

Japanese Office Action corresponding to Japanese Patent Application No. 1998/513794 dated Sep. 12, 2008.

FDA Alert updated Nov. 8, 2007 Erythropoiesis Stimulating Agents (ESA) (4 pages).

English translation of "Notice of Opposition" filed by Bioceuticals Arzneimittel AG 1-6 (2005) including the following D1-D9 annexed documents.

WO 98/10650 to East Carolina University Mar. 19, 1998 including International Search Report dated Oct. 24, 1997.
Rubins et al. "Metastatic Renal Cell Carcinoma" *Annals of Internal Medicine* 122(9):676-677 (1995).
Carlini et al. Recombinant human erythropoietin stumulates angiogenesis in vitro *Kidney International* 47:740-745 (1995).
Höckel et al. "Therapeutic Angiogenesis" *Arch Surg* 128:423-429 (1993).
Sungur, Cem "Renal Cell Carcinoma and Erythropoietin" *Annals of Internal Medicine* 123(9):732-733 (1995).
Anagnostou et al, "Erythropoietin has a mitogenic and positive chemotactic effect on endothelial cells" *Proc. Natl. Acad. Sci.* 87:5978-5982 (1990).
Carline et al. "Recombinant human erythropoietin (rHuEPO) increases endothelin-1 release by endothelial cells" *Kidney International* 43:1010-1014 (1993).
Nagai et al. "Effects of rHuEPO on cellular proliferation and endothelin-1 production in cultured endothelial cells" *Nephrol Dial Transplant* 10:1814-1819 (1995).
Yamaji et al. "Brain capillary endothelial cells express two forms of erythropoietin receptor mRNA" *Eur. J. Biochem* 239:494-500 (1996).
Miller et al. "Phase I-II Trial of Erythropoietin in the Treatment of Cisplatin-Associated Anemia" *J. Natl Cancer Inst* 84(2):98-103 (1992).
English translation of "Observations of Patentee in Reply" 22 pages (2006) including the following A1-A8 annexed documents.
Prescribing information for Procrit® (1-36) (2005).
BCCA Protocol Summary for Alpha-interferon (α-IFN) for Advanced Renal Cell Carcinoma (2006).
Neidhart, J.A. "Interferon therapy for treatment of renal cancer" *Cancer* 57(8 Suppl):1696-1699 (1986) ABSTRACT.
Whiteway et al. "An extremely delayed cytogenetic response to interferonalpha in a patient with chronic myeloidleukaemia" *Leukemia* 11(4):614-616 (1997).
<http://www.cancerguide.org/rcc_metastatic.html>1-4 (2006).
<http://www.noetic.org/research/sr/fags/html.>1-4 (2006).
English translation of "Response to the Patentee's Observations of 27th Apr. 2006" 1-17 (2006) including the following D11-D13 annexed documents.
Shinkelgaku et al. "Multiple cerebral infarction after treatment with cisplatin" *Rinsho Shinkeigaku* 36(3):499-502 (1996) ABSTRACT.
Ito et al. "Vitamin E prevents endothelial injury associated with cisplatin injection into the superior mesenteric artery of rats" *Heart Vessels* 10(4): 178-184 (1995) Abstract.
Breymann et al. "Optimal timing of repeated rh-erythropoietin administration improves its effectiveness in stimulating erythropoiesis in healthy volunteers" *Br J Haematol* 92(2):295-301 (1996) ABSTRACT.
English translation of "Opponent's Rule 71A EPC Submissions File" 1-40 2007.
English translation of Patentee's Rule 71(a) EPC Submissions 29 pages (2007) including the following A9-A13 annexed documents.
Expert Witness Statement of Professor Alexander F. Markham including his Curriculum Vitae 1-51 (2006).
Freed et al. "Idiopathic Regression of Metastases from Renal Cell Carcinoma" *The Journal of Urology* 118:538-542 (1977).

* cited by examiner

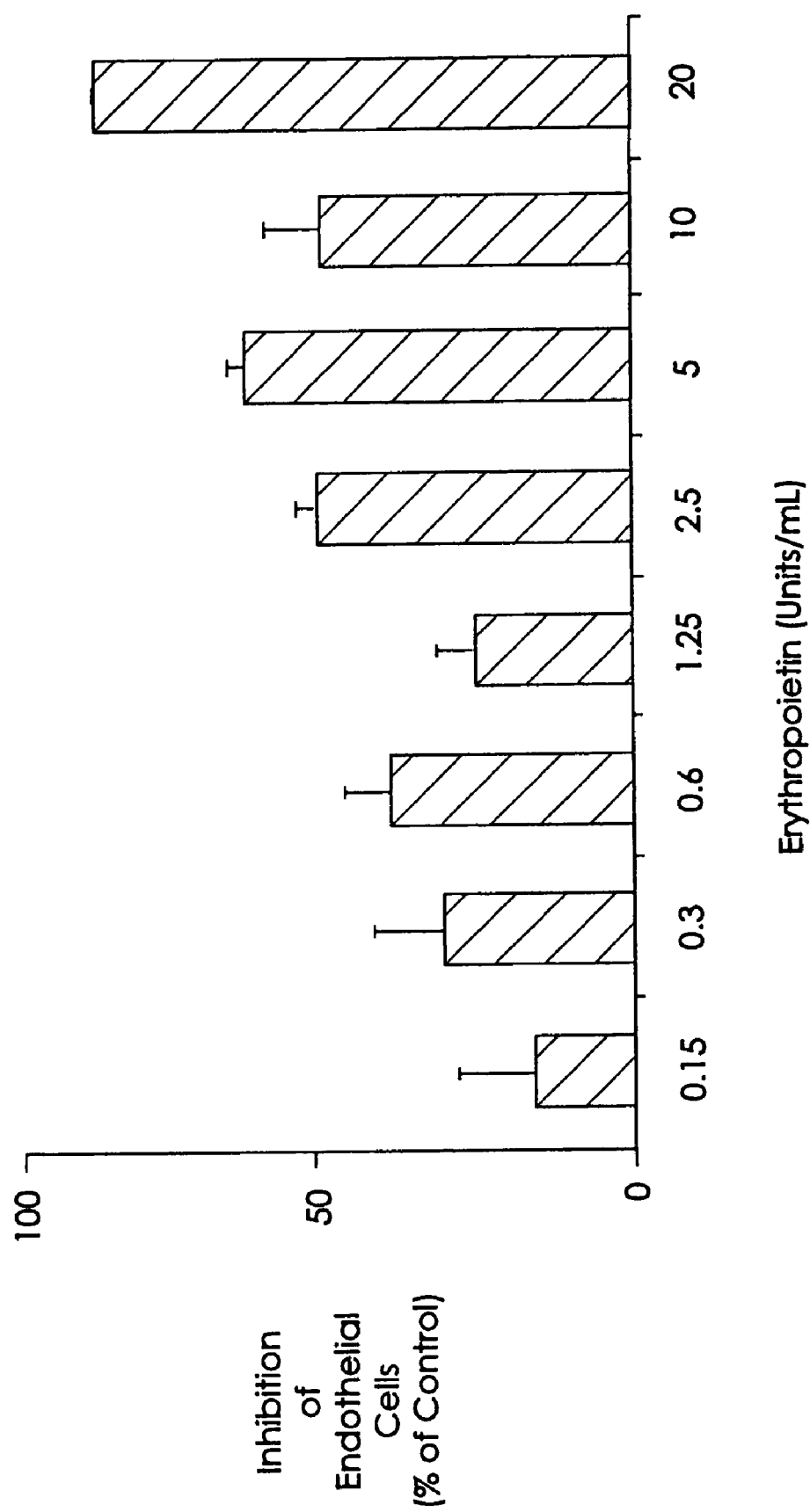

METHOD OF TREATING ENDOTHELIAL INJURY

This application is a divisional of Ser. No. 08/712,358, filed 11 Sep. 1996, now abandoned the disclosure of which is incorporated by reference herein in its entirety.

FIELD OF THE INVENTION

The present invention relates to the use of human erythropoietin (EPO) in the prevention or treatment of endothelial injury due to chemotherapy, radiation therapy, mechanical trauma, or to a disease state which damages the endothelium (such as inflammation, heart disease or cancer). The present invention further relates to the use of EPO in conjunction with chemotherapy.

BACKGROUND OF THE INVENTION

Erythropoietin (EPO) is a glycoprotein produced in the kidney, and is the principal hormone responsible for stimulating red blood cell production (erythrogenesis). EPO stimulates the division and differentiation of committed erythroid progenitors in the bone marrow. Normal plasma erythropoietin levels range from 0.01 to 0.03 Units/mL, and can increase up to 100 to 1.000-fold during hypoxia or anemia. Graber and Krantz, *Ann. Rev. Med.* 29:51 (1978); Eschbach and Adamson, *Kidney Intl.* 28:1 (1985). Recombinant human erythropoietin (rHuEpo or epoetin alfa) is commercially available as EPOGEN® (Amgen Inc., Thousand Oaks, Calif.) and as PROCRIT® (Ortho Biotech Inc., Raritan, N.J.). EPO is indicated for treatment of anemia, including anemias associated with cancer chemotherapy, chronic renal failure, malignancies, adult and juvenile rheumatoid arthritis, disorders of haemoglobin synthesis, prematurity, and zidovudine treatment of HIV infection.

The vascular endothelium is a layer of cells lining the inner vascular wall and in direct contact with blood, providing an active natural barrier between the circulatory and extravascular compartment. The endothelium is involved in signal and information transfer at the cellular, tissue and organ level, and plays a role in both cell-mediated and humoral immune responses. Endothelial cells are metabolically active and normally produce a number of substances with effects on the vascular lumen and on platelets. Endothelial vasodilators include prostacyclin ($PGI_2$) and endothelium-derived relaxing factor (EDRF, which may be nitric oxide or a more stable adduct thereof); these two substances also act to inhibit platelet aggregation.

Damage or destruction of the endothelium by physical trauma or disease processes such as atherosclerotic plaque formation may impair EDRF production, contributing to vasoconstriction. More diffuse and subtle endothelial damage, such as due to chronic hypertension or reperfusion after ischemia, also leads to altered EDRF production. Endothelial products localized to the luminal endothelial surface include ectoADPase and thrombomodulin. Vasoconstrictors released by the endothelium include endothelin. Endothelial cells also secrete growth factors which enhance endothelial mitogenesis and can induce new blood vessel formation (angiogenesis). It has been reported that granulocyte macrophage-colony stimulating factor (GM-CSF) and granulocyte-colony stimulating factor (G-CSF) stimulate proliferation and migration of endothelial cells. Interleukin-3 (IL-3) also enhances the proliferation of these cells. See Bussolino et al., *Nature* 337:471 (1989); Brizzi et al., *J. Clin. Invest.* 91:2887 (1993).

SUMMARY OF THE INVENTION

A first aspect of the present invention is a method of reducing endothelial injury caused by a chemotherapeutic agent, by administering an endothelial-protecting amount of erythropoietin in conjunction with the administration of the chemotherapeutic agent. The endothelial-protecting amount of erythropoietin may be administered simultaneously with the chemotherapeutic agent, prior to the chemotherapeutic agent, or after the chemotherapeutic agent.

A second aspect of the present invention is a method of enhancing endothelial cell inhibition in a subject treated with a chemotherapeutic agent, by administering an endothelial-inhibiting amount of erythropoietin in conjunction with the chemotherapeutic agent. The endothelial-inhibiting amount of erythropoietin may be administered simultaneously with, prior to, or after the chemotherapeutic agent.

A further aspect of the present invention is a method of treating a solid vascularized tumor by administering an anti-neoplastic chemotherapeutic agent in conjunction with an endothelial-inhibiting amount of erythropoietin. The endothelial-inhibiting amount of erythropoietin may be administered simultaneously with, prior to, or after the chemotherapeutic agent.

A further aspect of the present invention is a method of treating endothelial injury caused by mechanical damage, exposure to radiation, inflammation, heart disease or cancer by administering an endothelial-protecting amount of erythropoietin to a subject in need of such treatment.

The foregoing and other objects and aspects of the present invention are explained in detail in the specification set forth below.

BRIEF DESCRIPTION OF THE DRAWINGS

FIG. 4 is a graph showing the responses of endothelial cell cultures exposed first to varying dosages of EPO and, two hours later, to cisplatin (compared to control endothelial cell culture exposed only to cisplatin).

DETAILED DESCRIPTION OF THE INVENTION

Figure 1:
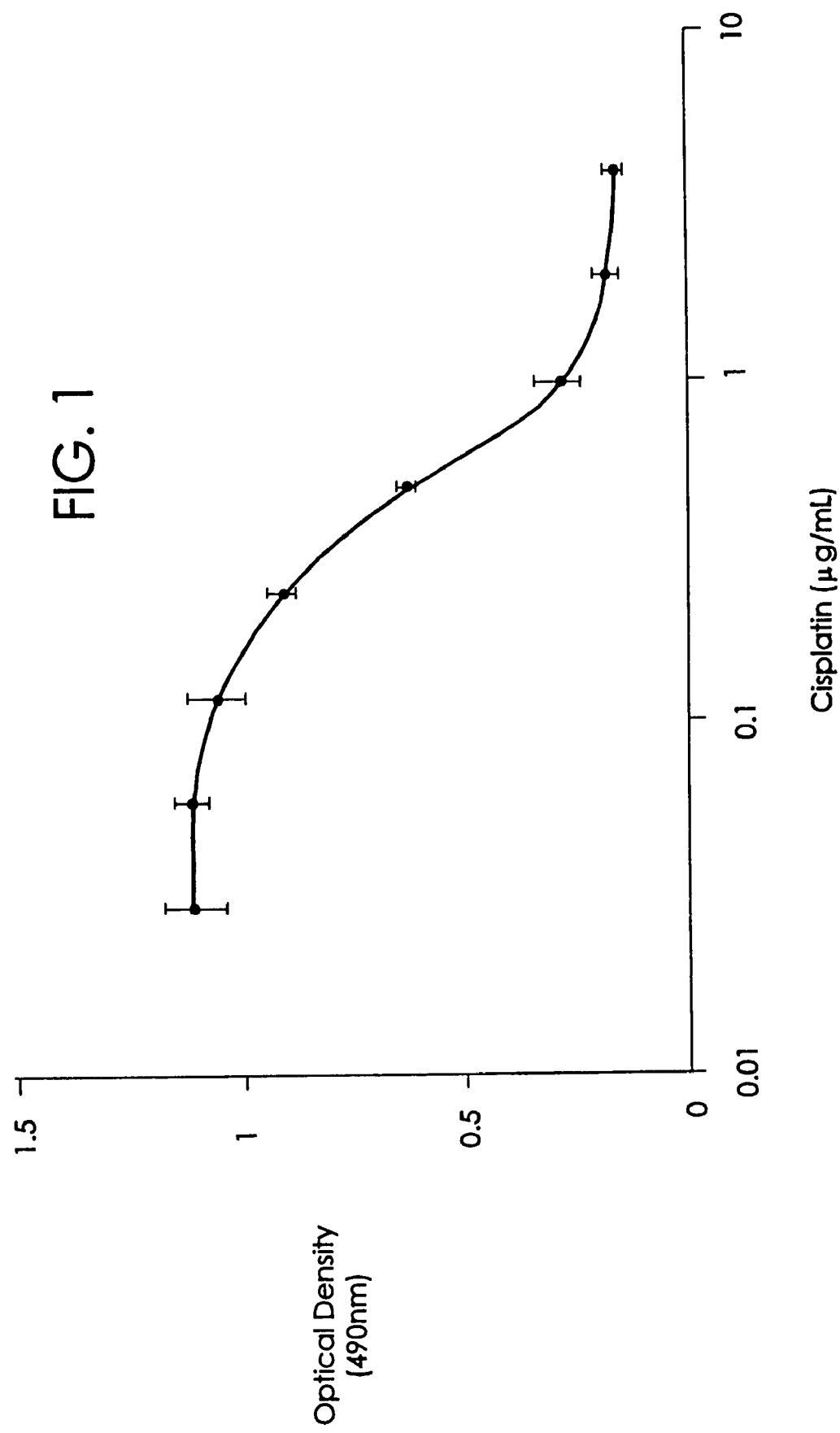
FIG. 1 is a graph showing the dose-response curve for viability of endothelial cells after exposure to cisplatin.

The present inventors have previously shown that recombinant human erythropoietin (EPO) exerts a mitogenic and chemoattractant (migratory) effect on human umbilical vein endothelial cells and bovine capillary endothelial cells. Anagnostou et al., *Proc. Natl. Acad. Sci. USA* 87:5978 (1990). Endothelial cell migration and proliferation are the key steps in the angiogenic process.

The present inventors have found that EPO can effectively prevent and/or repair endothelial damage caused by chemotherapeutic agents. The present inventors have found that administration of EPO concomitantly with chemotherapeutic agents produces a biphasic response: certain doses of EPO protect endothelial cells from the deleterious effects of the chemotherapeutic agent, while increased doses enhance the endothelial growth-suppression caused by the chemotherapeutic agent.

The use of EPO to enhance endothelial growth-suppression during chemotherapy is useful in treating angiogenic tumors, where it is desirable to prevent or slow the formation of new blood vessels which support tumor growth. Tumors require an adequate blood supply, and growth of new vessels in the tumor mass is stimulated by angiogenic factors secreted by tumor tissue. In animal models, inhibition of angiogenesis in tumor tissue has been shown to cause tumor regression. Highly vascularized solid tumors include cerebellar hemangioblastoma, ductal carcinoma of the breast, and squamous cell cancer of the larynx. Abnormal angiogenesis is involved in additional pathological conditions, including diabetic retinopathy, neovascular glaucoma, rheumatoid arthritis, and psoriasis. The ability of EPO to reduce or prevent abnormal angiogenesis will be of use in preventing or reducing angiogenesis associated with such disease states.

One method according to the present invention is the use of EPO as an adjunct in the chemotherapy of neoplastic disease. EPO is provided in endothelial-protecting amounts where protection of the endothelium from the adverse effects of chemotherapeutic agents is desired. A second method according to the present invention is the use of EPO as an adjunct in the chemotherapy of neoplastic disease, where enhancement of the adverse effects of chemotherapeutic agents on endothelium (e.g., enhancement of endothelial growth suppression) is desired. In such situations, EPO is provided in endothelial-inhibiting amounts.

As used herein, endothelial-protecting amounts of EPO refer to those dosages which reduce or prevent the suppression of endothelial growth which would otherwise occur due to exposure to a chemotherapeutic agent or radiation, mechanical trauma, or a disease state known to damage the endothelium. Alternatively, an endothelial-protecting amount of EPO may be defined as those dosages which increase the numbers of viable endothelial cells following exposure to the chemotherapeutic agent or radiation, mechanical trauma, or a disease state known to damage the endothelium; the increased number of viable cells is in comparison to that which would be expected in the absence of EPO. The most effective endothelial-protecting amounts of EPO may vary depending upon the time of administration and the etiology of endothelial damage.

Where endothelial damage is due to exposure to a chemotherapeutic agent, the most effective endothelial-protecting amounts of EPO will vary depending upon whether EPO is administered simultaneously with, prior to, or after, the chemotherapeutic agent, and may vary depending upon the specific chemotherapeutic agent in question.

As used herein, endothelial-inhibiting amounts of EPO refer to those dosages which enhance or increase the suppression of endothelial growth which would otherwise occur due to exposure to a chemotherapeutic agent or radiation, mechanical trauma, or a disease state known to damage the endothelium. Alternatively, an endothelial-inhibiting amount of EPO may be defined as those dosages which decrease the numbers of viable endothelial cells following exposure to the chemotherapeutic agent or radiation, mechanical trauma, or a disease state known to damage the endothelium; the decreased number of viable cells is in comparison to that which would be expected in the absence of EPO. The most effective endothelial-inhibiting amounts of EPO may vary depending upon the time of administration and the etiology of endothelial damage.

Where endothelial damage is due to exposure to a chemotherapeutic agent, the most effective inhibiting amounts of EPO will vary depending upon whether EPO is administered simultaneously with, prior to, or after, the chemotherapeutic agent, and may vary depending upon the specific chemotherapeutic agent in question.

Endothelial damage may be assessed by a reduction in the proliferation of endothelial cells and/or decreased numbers of viable endothelial cells, leading to a total decrease in the number of viable endothelial cells. Such a decrease in the number of viable endothelial cells may also be referred to as endothelial growth suppression, or endothelial cell suppression or inhibition.

As used herein, a method of reducing endothelial injury in a subject caused by administration of a chemotherapeutic agent to the subject refers to a method which reduces or prevents the decrease in viable endothelial cells which would otherwise be caused by administration of the chemotherapeutic agent. As used herein, a method of enhancing endothelial cell inhibition in a subject caused by administration of a chemotherapeutic agent to the subject refers to a method which increases or enhances the reduction in viable endothelial cells which would otherwise be caused by administration of the chemotherapeutic agent.

Damage to endothelial cells may also be caused by radiation therapy, mechanical trauma, and by disease states such as inflammation, heart disease (e.g., atherosclerosis) and cancer. In atherosclerosis, for example, injury to or dysfunction of the endothelium leads to reduced vasodilator response and to increased platelet deposition on the arterial wall. Serotonin and thromboxane $A_2$ released from deposited platelets cause arterial constriction and spasm, increase adhesion and aggregation of platelets, and enhance the atherosclerotic process. The consequences of coronary obstruction are often ameliorated by the formation of new coronary vessels in response to angiogenic stimuli. The use of EPO to enhance endothelial growth and/or repair, or to prevent endothelial damage, will be a useful adjunct in treating endothelial damage due to mechanical damage, radiation therapy, or due to disease states which adversely affect the endothelium.

As used herein, human erythropoietin (EPO) refers to both the naturally occurring human erythropoietin glycoprotein as well as recombinant human erythropoietin (rHuEpo or epoetin alfa, available commercially as EPOGEN® (Amgen Inc., Thousand Oaks, Calif.) and as PROCRIT® (Ortho Biotech Inc., Raritan, N.J.)). Peptide analogs of EPO may also be used in the methods of the present invention. As used herein, peptide analogs are those compounds which, while not having amino acid sequences identical to that of EPO, have a similar three-dimensional structure. In protein molecules which interact with a receptor, the interaction takes place at the surface-accessible sites in a stable three-dimensional molecule. By arranging the critical binding site residues in an appropriate conformation, peptides which mimic the essential surface features of EPO binding region may be designed and synthesized in accordance with known techniques. A molecule which has a surface region with essentially the same molecular topology to the binding surface of EPO will be able to mimic the interaction of EPO with the EPO receptor. Methods for determining peptide three-dimensional structure and analogs thereto are known, and are sometimes called 'rational drug design techniques'. See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock (applicants specifically intend that the disclosures of all U.S. patents cited herein be incorporated by reference in their entirety).

Peptides which mimic the biological activity of erythropoietin (EPO receptor peptide ligands) may be substituted for EPO in the methods of the present invention. The sequence of such peptides may represent fragments of the full-length EPO protein sequence, which fragments are capable of binding to and activating the EPO receptor. Additionally, peptides with sequences dissimilar to that of EPO may be utilized in the methods of the present invention, where such peptides mimic the biological activity of EPO. Wrighton et al. report the identification and characterization of small peptides that bind to and activate the erythropoietin receptor on the surface of target cells, although the peptides' sequences are not similar to the primary sequence of EPO (Wrighton et al., *Science* 273:458 (26 Jul. 1996)). These peptide agonists are represented by a 14-amino acid disulfide-bonded cyclic peptide with an identified minimum consensus sequence. The structure of a complex of one such peptide mimetic with the erythropoietin receptor is described by Livnah et al., *Science* 273:464 (26 Jul. 1996).

As used herein, the term chemotherapeutic agent refers to cytotoxic antineoplastic agents, that is, chemical agents which preferentially kill neoplastic cells or disrupt the cell cycle of rapidly proliferating cells, used therapeutically to prevent or reduce the growth of neoplastic cells. Chemotherapeutic agents are also known as antineoplastic drugs or cytotoxic agents, and are well known in the art. As used herein, chemotherapy includes treatment with a single chemotherapeutic agent or with a combination of agents. In a subject in need of treatment, chemotherapy may be combined with surgical treatment or radiation therapy, or with other antineoplastic treatment modalities.

Exemplary chemotherapeutic agents are vinca alkaloids, epipodophyllotoxins, anthracycline antibiotics, actinomycin D, plicamycin, puromycin, gramicidin D, paclitaxel (TAXOL®, Bristol Myers Squibb), colchicine, cytochalasin B, emetine, maytansine, and amsacrine (or "mAMSA"). The vinca alkaloid class is described in *Goodman and Gilman's The Pharmacological Basis of Therapeutics,* 1277-1280 (7th ed. 1985) (hereafter "Goodman and Gilman"). Exemplary of vinca alkaloids are vincristine, vinblastine, and vindesine. The epipodophyllotoxin class is described in Goodman and Gilman, supra at 1280-1281. Exemplary of epipodophyllotoxins are etoposide, etoposide orthoquinone, and teniposide. The anthracycline antibiotic class is described in Goodman and Gilman, supra at 1283-1285. Exemplary of anthracycline antibiotics are daunorubicin, doxorubicin, mitoxantraone, and bisanthrene. Actinomycin D, also called Dactinomycin, is described in Goodman and Gilman, supra at 1281-1283. Plicamycin, also called mithramycin, is described in Goodman and Gilman, supra at 1287-1288. Additional chemotherapeutic agents include cisplatin (PLATINOL®, Bristol Myers Squibb); carboplatin (PARAPLATIN®, Bristol Myers Squibb); mitomycin (MUTAMYCIN®, Bristol Myers Squibb); altretamine (HEXALEN®, U.S. Bioscience, Inc.); cyclophosphamide (CYTOXAN®, Bristol Myers Squibb); lomustine [CCNU] (CEENU®, Bristol Myers Squibb); carmustine [BCNU] (BICNU®, Bristol Myers Squibb).

Methods of administering chemotherapeutic drugs vary depending upon the specific agent used, as would be known to one skilled in the art. Depending upon the agent used, chemotherapeutic agents may be administered, for example, by injection (intravenously, intramuscularly, intraperitoneally, subcutaneously, intratumor, intrapleural) or orally.

As used herein, the administration of a compound "in conjunction with" a second compound means that the two compounds are administered closely enough in time that the presence of one alters the biological effects of the other. The two compounds may be administered simultaneously (concurrently) or sequentially. Simultaneous administration may be carried out by mixing the compounds prior to administration, or by administering the compounds at the same point in time but at different anatomic sites or using different routes of administration.

The phrases "concurrent administration", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Subjects to be treated by the method of the present invention include both human and animal (e.g., dog, cat, cow, horse) subjects, and are preferably mammalian subjects.

Many chemotherapeutic agents act at specific phases of the cell cycle, and are active only against cells in the process of division. Neoplasms which are the most susceptible to chemotherapy are those with a high percentage of cells in the process of division, including but not limited to breast, liver, brain, lung, and ovarian cancer. Highly vascularized solid tumors are amenable to treatment with endothelial-inhibiting amounts of EPO in conjunction with chemotherapeutic agents, as these tumors rely on angiogenesis to provide adequate blood supply to the growing tumor tissue.

EPO used according to the methods of the present invention may be administered by any suitable means, as would be apparent to one skilled in the art. EPO may be administered systemically (e.g., intravenously) or locally (e.g., injected into a tumor, tissues immediately surrounding a tumor, or into an anatomic compartment containing a tumor). For example, where an endothelial-inhibiting amount of EPO is utilized as an adjunct to chemotherapy, the EPO may be administered locally to a tumor (or the immediately surrounding tissue) in which it is desirable to prevent angiogenesis. Where a chemotherapeutic agent is delivered systemically, for example, an endothelial-protecting amount of EPO may be administered systemically by intravenous injection.

The dosage and timing of EPO administration used in conjunction with a chemotherapeutic agent will similarly depend upon the desired effect. The present inventors have discovered that depending upon the timing of EPO administration (simultaneous with, before, or after chemotherapeutic agent administration) and the dosage of EPO, EPO either protects the endothelium from the growth-inhibiting effects of chemotherapeutic agents, or enhances the endothelial growth inhibition seen with chemotherapeutic agents. It will be apparent to those skilled in the art how to determine, by routine experimentation, the dosage and timing of EPO administration in conjunction with a particular chemotherapeutic agent to achieve a desired effect.

The maximum amount of EPO that can be administered in single or multiple doses has not been determined. Doses of up to 1,500 Units/kg for three to four weeks have been administered without toxic effects due to EPO itself. Eschbach et al., in: *Prevention of Chronic Uremia* (Friedman et al., eds.), Field and Wood Inc., Philadelphia, pp. 148-155 (1989). In the present methods, where it is desired to protect the endothelium from the endothelial damage and/or endothelial growth suppression caused by a chemotherapeutic agent, EPO is administered in an endothelial-protecting amount. Suitable endothelial-protecting dosages may range from about 100 U/kg to about 200 U/kg. In the present methods, where it is desired to enhance the endothelial damage and/or endothelial growth suppression caused by a chemotherapeutic agent, EPO is administered in an endothelial-inhibiting amount which may range from about 750 U/kg to about 2,000 U/kg. As noted above, the dosage and timing of EPO administration used in conjunction with a chemotherapeutic agent will depend upon the desired effect, as well as the chemotherapeutic agent utilized.

The following examples are provided to illustrate the present invention, and should not be construed as limiting thereof.

EXAMPLE 1

Materials and Methods

Cell Culture. Human umbilical vein endothelial cells (HUVECs) were obtained from Caesarian section derived cords. HUVECs were cultured by standard methodology in 25 cm$^2$ T-flasks (Corning Inc., Corning, N.Y.) coated with 0.5 porcine skin gelatin (Sigma Chemical Co., St. Louis, Mo.). Medium 199 (Life Technologies, Gaithersburg, Md.), supplemented with 20% defined fetal bovine serum (FBS) (Hyclone, Logan, Utah), 16 U/ml heparin (Sigma), 50 µg/ml bovine hypothalamus derived endothelial mitogen (Biomedical Technologies, Stoughton, Mass.), 100 U/ml penicillin and 100 µg/ml streptomycin was used for the growth of HUVECs. Endothelial cells were characterized by homogenous and typical cobblestone morphology, von Willebrand factor antigen positivity, and the presence of Weibel-Palade bodies, as are known in the art.

Protection/Inhibition Assay. The number of metabolically active cells after exposure of endothelial cell cultures to test agents was assessed using a calorimetric method. This assay utilizes solutions of a tetrazolium compound [3-(4,5-dimethylthiazol-2-yl)-5-(3-carboxymethoxyphenyl)-2-(4 Sulfophenyl)-2H-tetrazolium] (MTS) and an electron coupling reagent, phenazine methosulfate (PMS; available from Promega Corp., Madison, Wis.). See Denizot and Lang, *J. Immunol. Methods* 89:271 (1986); Promega Corporation Technical Bulletins 112, 152 and 169). MTS is bioreduced into a formazan by dehydrogenase enzymes found in metabolically active cells. The amount of formazan is measured at 490 nm absorbance and is directly proportional to the numbers of living cells in culture.

Endothelial cells grown in the complete (supplemented) M199 medium were harvested in the log phase. At 80-90% confluency, EC culture monolayers were washed with phosphate buffered saline (PBS), treated with 0.25% trypsin in 1 mM EDTA for 1-2 minutes, and then the cells were suspended in complete medium. The number and viability of the cells was determined using a hemocytometer and the trypan blue staining, respectively. Cell suspensions of 7.22×10$^4$ cells/ml medium were prepared and 90 µl (6.5×10$^3$ cells) were dispensed into each well of a 96-well plate. After overnight incubation at 37° C., 5% CO$_2$, in a humidified atmosphere, EPO and/or the chemotherapeutic agent were added at concentrations and in the order specified in the examples described below. Plates were then incubated for another 24 hours. At the end of this incubation period, 20 µl of freshly prepared combined MTS/PMS (20:1 ratio) solution was added into each well and the plates were incubated for 1-4 more hours, as per manufacturer's recommendations. The absorbance of each well at 490 nm was recorded using an ELISA plate reader. The LD50 and the effect of the various treatments on cell viability and chemosensitivity were determined by plotting the corrected absorbance at 490 nm versus the concentration of the additive (EPO, chemotherapeutic agent, or combinations thereof).

Statistical Considerations. For protection/inhibition assays, experiments were performed in triplicate. All other experiments were performed at least five times. Results were averaged and means ±SD reported. Controls for all experiments included one to two triplicate wells treated with each of the following:
1) 1 µg/ml cisplatin;
2) 50 µg/ml cisplatin;
3) 10 or 20 U/ml of EPO;
4) 0.6 or 1.2 U/ml of EPO.

Thus for each experiment, three to six wells received the above four control treatments (total 12-24 control wells). An additional control consisting of a triplicate well of untreated cells was also performed.

EXAMPLE 2

Determination of Cisplatin LD50

Ninety-six-well plates containing endothelial cells were prepared as described in Example 1 and incubated overnight at 37° C., 5% CO$_2$, in a humidified atmosphere. A solution of 160 µg/ml cisplatin was prepared, and serial dilutions were added to the wells (5 µl per well; concentrations varied from 0.03125 µg/ml to 4.0 µg/ml. The plates were then incubated for two days (48 hours) and viability of endothelial cells was assessed using the MTS/PMS technique described in Example 1. The absorbance of each well at 490 nm was recorded using an ELISA plate reader. The corrected absorbance at 490 nm versus the concentration of cisplatin (µg/mL) was plotted (FIG. 1) to provide a dose-response curve. The concentration of cisplatin required to give 50% of the maximal response (LD50 of cisplatin) was determined to be 0.45 µg/ml.

In view of the above findings, a dosage of 1 µg/ml of cisplatin was used to determine the effects of EPO on endothelial cells, as provided in the following examples.

EXAMPLE 3

Effects of Simultaneous Cisplatin and EPO on Endothelial Cells

To determine the effects of combined EPO and cisplatin on endothelial cells, serial dilutions of EPO were added to endothelial cell cultures simultaneously with cisplatin.

Endothelial cell cultures were prepared as described in Example 1. Cisplatin (final concentration of 1 µg/ml) was added to each test well simultaneously with 5 µl of various EPO preparations (final EPO concentration ranging from 0.15 to 20 U/ml. Endothelial cell viability was assessed using the MTS/PMS calorimetric assay described in Example 1. Results were compared to control wells (endothelial cells treated with 1 µg/ml cisplatin alone, considered as the baseline and represented in FIG. 2 as 0%). Results are provided in FIG. 2; the "% of control" is the percentage change of optical density at 490 nm over the control, such that "0%" indicates the test well had similar numbers of metabolically active cells as the control, whereas "50%" indicates 50% more and "−50%" indicates 50% fewer metabolically active cells.

Figure 2:
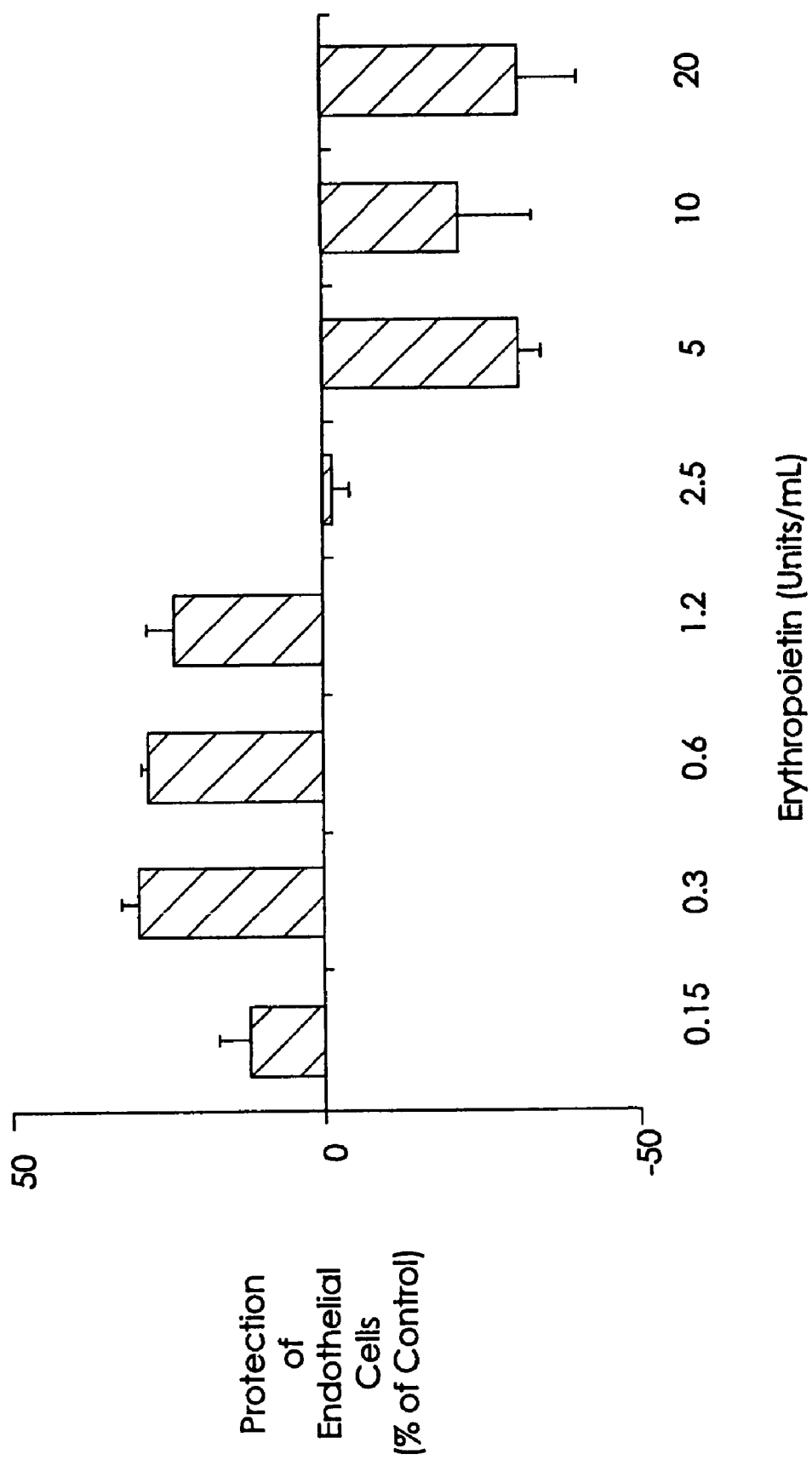
FIG. 2 is a graph showing the responses of endothelial cell cultures exposed simultaneously to cisplatin and varying dosages of EPO, compared to control endothelial cell cultures exposed only to cisplatin.

As shown in FIG. 2, a biphasic response was observed when EPO was added to cell cultures simultaneously with the addition of cisplatin. Endothelial cell cultures treated with from 0.15 to 1.25 U/ml of EPO were protected from the damaging effects of cisplatin when EPO was added simultaneously with cisplatin. EPO concentrations of 0.3 U/ml provided the greatest protection of endothelial cells when EPO was added simultaneously with cisplatin; the number of viable cells was approximately 30% greater than that observed in control cultures treated with cisplatin only.

As also shown in FIG. 2, endothelial cell growth was inhibited in cultures treated with from 5 to 20 U/ml of EPO when EPO was added simultaneously with cisplatin, compared to cultures treated with cisplatin alone. Cultures treated with 5 U/ml of EPO and 1 µg/ml cisplatin showed a 33% decrease in the number of viable cells compared to control cells exposed to cisplatin alone.

EXAMPLE 4

Effects of EPO on Endothelial Cells Administered after Cisplatin Exposure

In this experiment, serial dilutions of EPO were added to endothelial cell cultures two hours after the cultures were exposed to cisplatin.

Endothelial cell cultures were prepared as described in Example 1. Cisplatin was added to each test well (1 µg/ml final concentration of cisplatin); two hours later 5 µl of an EPO preparation ranging from 0.15 to 20 U/ml final concentration was added. Endothelial cell viability was assessed using the MTS/PMS calorimetric assay described in Example 1. Results were compared to control wells (endothelial cells treated with 1 µg/ml cisplatin alone).

Figure 3:
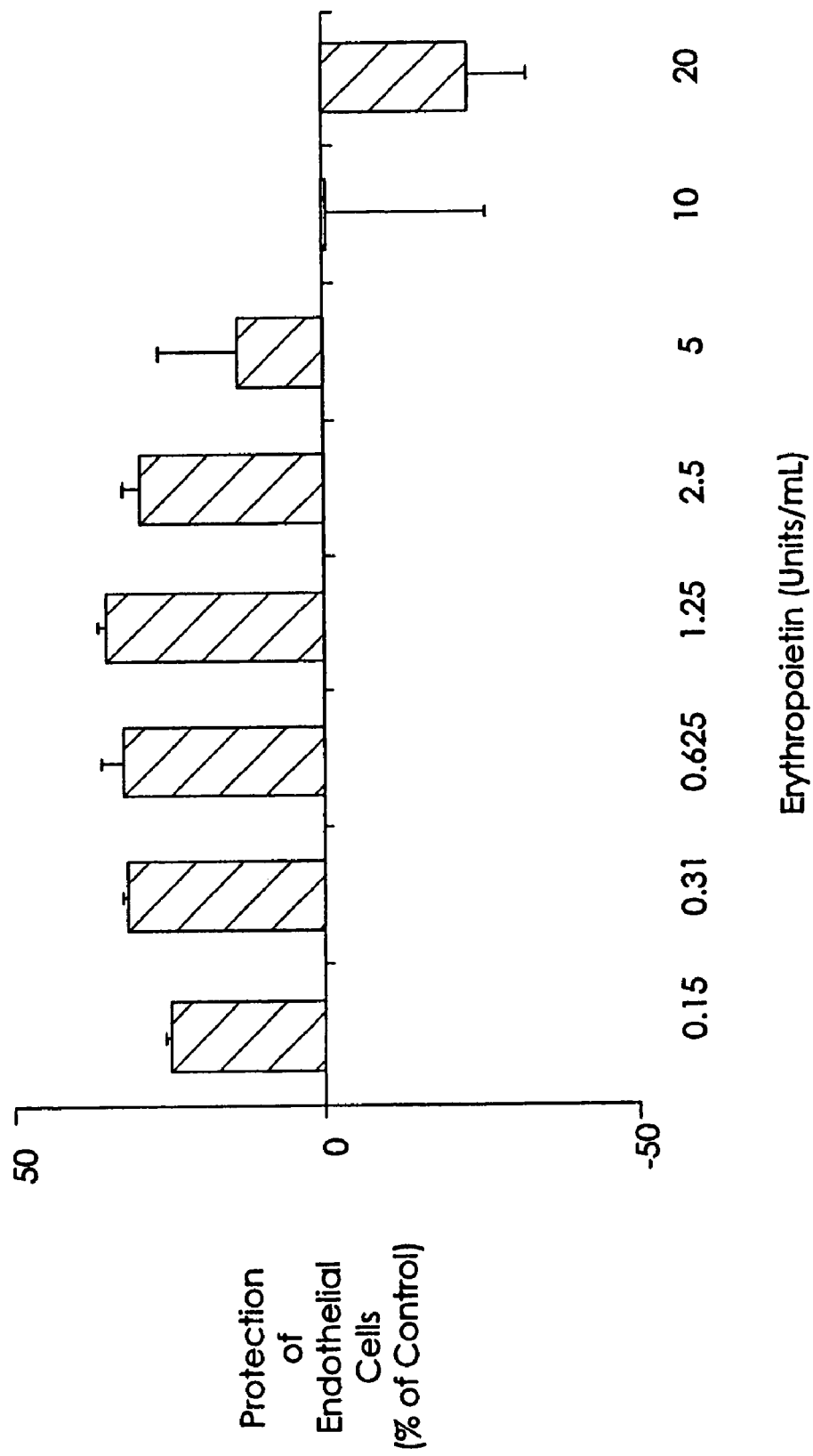
FIG. 3 is a graph showing the responses of endothelial cell cultures exposed first to cisplatin and, two hours later, to varying dosages of EPO (compared to control endothelial cell cultures exposed only to cisplatin).

Results are provided in FIG. 3, and show that a biphasic response was observed when EPO was added to cell cultures after the addition of cisplatin. Endothelial cell cultures treated with from 0.15 to 5 U/ml of EPO were protected from the damaging effects of cisplatin when EPO was added two hours following cisplatin exposure. The number of viable cells after treatment with 1.25 U/ml EPO after cisplatin exposure was 34% greater than that of controls. In contrast, cell viability in the presence of 10 to 20 U/ml EPO administered two hours after cisplatin exposure was reduced over that seen in controls (cisplatin only).

EXAMPLE 5

Effects of EPO on Endothelial Cells Administered Prior to Cisplatin Exposure

In this experiment, serial dilutions of EPO were added to endothelial cell cultures two hours before the cultures were exposed to cisplatin.

Endothelial cell cultures were prepared as described in Example 1. Each test well received 5 µl of an EPO preparation ranging from 0.15 to 20 U/ml EPO; two hours later cisplatin was added to each test well (5 µl of 1 µg/ml cisplatin). Endothelial cell viability was assessed using the MTS/PMS calorimetric assay described in Example 1. Results were compared to control wells (endothelial cells treated with 1 µg/ml cisplatin alone).

Results are provided in FIG. 4, and show a reduction in the number of viable endothelial cells after exposure to EPO two hours prior to cisplatin exposure (compared to control cells exposed only to cisplatin). Cell proliferation and viability was decreased by as much as 81% compared to controls. The inhibition was dose dependent; EPO concentrations as low as 5 and 2.5 U/ml reduced cell growth by 58% and 48%, respectively, compared to controls.

The foregoing is illustrative of the present invention and is not to be construed as limiting thereof. The invention is defined by the following claims, with equivalents of the claims to be included therein.

The invention claimed is:

1. A method of treating a solid vascularized tumor in a subject in need of such treatment, comprising administering erythropoietin prior to administration of cisplatin, carboplatin or mitomycin, wherein said erythropoietin is administered in an amount effective to enhance suppression of endothelial growth associated with administration of said cisplatin, carboplatin or mitomycin, wherein said amount is a dosage in a range of 750 Units per kilogram to 2000 Units per kilogram.

2. A method according to claim 1, wherein said cisplatin, carboplatin or mitomycin is administered intravenously.

3. A method according to claim 1, wherein said erythropoietin is administered intravenously or subcutaneously.

4. A method according to claim 1, wherein said cisplatin, carboplatin or mitomycin is administered in a manner selected from the group consisting of intravenous, intramuscular, intraperitoneal, subcutaneous, intratumor, and intrapleural injection.

5. A method of treating a solid vascularized tumor according to claim 1, wherein said subject is afflicted with a solid vascularized tumor selected from cerebellar hemangioblastoma, ductal carcinoma of the breast or squamous cell cancer of the larynx.

6. A method of treating a solid vascularized tumor according to claim 5, wherein the solid vascularized tumor is a cerebellar hemangioblastoma.

7. A method of treating a solid vascularized tumor according to claim 5, wherein the solid vascularized tumor is a ductal carcinoma of the breast.

8. A method of treating a solid vascularized tumor according to claim 5, wherein the solid vascularized tumor is a squamous cell cancer of the larynx.

9. A method of treating a solid vascularized tumor in a subject in need of such treatment, comprising administering erythropoietin prior to administration of cisplatin;
   wherein said erythropoietin is administered in an endothelial-growth suppressing amount, wherein said amount is a dosage in a range from about 750 Units per kilogram to about 2,000 Units per kilogram.

10. A method according to claim 9, wherein said cisplatin is administered intravenously.

11. A method according to claim 9, wherein said erythropoietin is administered intravenously or subcutaneously.

12. A method of treating a solid vascularized tumor according to claim 9, wherein said subject is afflicted with a solid vascularized tumor selected from cerebellar hemangioblastoma, ductal carcinoma of the breast, or squamous cell cancer of the larynx.

* * * * *

UNITED STATES PATENT AND TRADEMARK OFFICE
CERTIFICATE OF CORRECTION

PATENT NO. : 7,531,501 B1  Page 1 of 1
APPLICATION NO. : 09/525797
DATED : May 12, 2009
INVENTOR(S) : Anagnostou et al.

It is certified that error appears in the above-identified patent and that said Letters Patent is hereby corrected as shown below:

Title Page, Item (*) Notice: Please add -- This patent is subject to a terminal disclaimer --

Title Page 2, Left Column line 13, Carlini: Please add -- 1993 -- after "1010-1014."

Title Page 2, Left Column line 62, Carlini et al.:
Please correct "Scoiety" to read -- Society --

Title Page 2, Right Column line 44, Taylor et al.:
Please correct "erthropoitin" to read -- erythropoietin --

Title Page 2, Right Column line 61, Nagai, T.:
Please correct "endothelian" to read -- endothelial --

Title Page 3, Left Column line 5, Carlini:
Please correct "stumulates" to read -- stimulates --

Title Page 3, Left Column line 14 Carline et al.:
Please correct "Carline" to read -- Carlini --

Signed and Sealed this

Fourteenth Day of July, 2009

JOHN DOLL
*Acting Director of the United States Patent and Trademark Office*